United States Patent
Obayashi et al.

(10) Patent No.: US 6,884,915 B2
(45) Date of Patent: Apr. 26, 2005

(54) PROCESS FOR PRODUCING STYRENE

(75) Inventors: Shuji Obayashi, Mie (JP); Takahito Nishiyama, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 270 days.

(21) Appl. No.: 10/124,318

(22) Filed: Apr. 18, 2002

(65) Prior Publication Data

US 2002/0165418 A1 Nov. 7, 2002

Related U.S. Application Data

(63) Continuation of application No. PCT/JP01/07091, filed on Aug. 17, 2001.

(30) Foreign Application Priority Data

| Aug. 18, 2000 | (JP) | ................................... | 2000-248094 |
| Sep. 6, 2000 | (JP) | ................................... | 2000-269612 |
| Sep. 6, 2000 | (JP) | ................................... | 2000-269613 |

(51) Int. Cl.$^7$ ................................................ C07C 2/64
(52) U.S. Cl. ........................ 585/444; 585/441; 585/443
(58) Field of Search ................................ 585/441, 444, 585/443

(56) References Cited

U.S. PATENT DOCUMENTS 6,388,154 B1 * 5/2002 Hamana et al. ............. 585/441
6,461,995 B1 * 10/2002 Addiego et al. ............ 502/304

FOREIGN PATENT DOCUMENTS

| EP | 0 323 115 | 7/1989 |
| JP | 58-89945 | 5/1983 |
| WO | WO 99/03806 | 1/1999 |

* cited by examiner

*Primary Examiner*—Thuan D Dang
(74) *Attorney, Agent, or Firm*—Oblon, Spivak, McClelland, Maier & Neustadt, P.C.

(57) ABSTRACT

The present invention is a process for producing styrene by dehydrogenation of ethylbenzene, which contains the steps of (i) feeding a raw material gas containing ethylbenzene and steam to a first dehydrogenating step to produce a reacted gas containing ethylbenzene, styrene and hydrogen in the presence of a dehydrogenation catalyst, (ii) feeding the reacted gas obtained in the first dehydrogenating step to an oxidizing step to combust at least part of hydrogen in the presence of an oxidation catalyst, and (iii) feeding the reacted gas obtained in the oxidizing step to a second dehydrogenating step to produce styrene from ethylbenzene in the presence of the dehydrogenation catalyst, with maintaining the carbon dioxide-generating ratio in the second dehydrogenating step at a level less than 2.1 times that at the initial stage of the reaction.

19 Claims, No Drawings

PROCESS FOR PRODUCING STYRENE

This application is a Continuation of International Application No. PCT/JP01/07091 Filed on Aug. 17, 2001

TECHNICAL FIELD

The present invention relates to an improvement of a process for producing styrene by dehydrogenating ethylbenzene. The invention enables to produce styrene with maintaining a high yield and a high selectivity over a long period of time.

BACKGROUND ART

Production of styrene by dehydrogenation of ethylbenzene is commonly conducted by mixing ethylbenzene with steam and passing the mixture through a dehydrogenation catalyst-packed bed. Since the dehydrogenation reaction of ethylbenzene is an endothermic reaction, temperature decreases with the progress of the reaction. In addition, hydrogen generated by the dehydrogenation reaction increases the concentration of hydrogen in the produced gas. These changes adversely affect the dehydrogenation reaction, and hence, the reaction rate is gradually lowered with the progress of the reaction.

In order to solve the above-described problems, there have conventionally been proposed a method of mixing the reaction-produced gas effused from the dehydrogenation catalyst-packed bed with oxygen, passing the mixed gas through an oxidation catalyst-packed bed to selectively combust hydrogen in the reaction-produced gas, and again passing through the dehydrogenation catalyst-packed bed (see Japanese Patent Laid-Open Nos. 130531/1985 and 225140/1986).

According to this method, the reaction-generated gas effused from the oxidation catalyst-packed bed contains a decreased concentration of hydrogen and is at an elevated temperature due to the heat generated by the combustion of hydrogen, and hence the dehydrogenation reaction can again be conducted at a high reaction rate. Therefore, use of a reaction apparatus wherein the dehydrogenation reaction-packed bed and the oxidation catalyst-packed bed are disposed alternately enables to finally attain an extremely high conversion of ethylbenzene.

However, one of the problems with the process of producing styrene by dehydrogenation of ethylbenzene using the combination of dehydrogenation reaction and oxidation reaction is that yield of styrene is seriously reduced after a long period of operation.

DISCLOSURE OF THE INVENTION

A subject of the invention is to provide a process for producing styrene from ethylbenzene containing a combination of dehydrogenation reaction and oxidation reaction wherein styrene can be produced with a high yield over a long period of time.

As a result of intensive investigations on the above-described subject, the inventors have found that styrene can be produced stably with a high yield over a long period of time by maintaining the carbon dioxide-generating ratio in the dehydrogenation step at a level less than 2.1 times that at the initial stage of the reaction, thus having achieved the invention based on the finding.

That is, one aspect of the invention lies in a process for producing styrene by dehydrogenation of ethylbenzene, which contains the steps of (i) feeding a raw material gas containing ethylbenzene and steam to a first dehydrogenating step to produce a reacted gas containing ethylbenzene, styrene and hydrogen in the presence of a dehydrogenation catalyst, (ii) feeding the reacted gas obtained in the first dehydrogenating step to an oxidizing step to combust at least part of hydrogen in the presence of an oxidation catalyst, and (iii) feeding the reacted gas obtained in the oxidizing step to a second dehydrogenating step to produce styrene from ethylbenzene in the presence of the dehydrogenation catalyst, with maintaining the carbon dioxide-generating ratio in the second dehydrogenating step at a level less than 2.1 times that at the initial stage of the reaction.

Another aspect of the invention lies in a process for producing styrene by dehydrogenation of ethylbenzene in the presence of a potassium-containing, iron-based catalyst, which contains filling a catalyst showing a lower potassium-flying rate in the upstream portion of the catalyst-packed bed within the dehydrogenation reactor.

BEST MODE FOR CARRYING OUT THE INVENTION

The step to be used in the process of the invention for producing styrene by dehydrogenation of ethylbenzene is a step wherein two or more dehydrogenating steps are connected in series. To be specific, in the step wherein 2, 3 or 4 dehydrogenating steps are connected in series, there may be provided a dehydrogenating step or steps in parallel. In addition, an oxidizing step may be provided between any two dehydrogenating steps connected. In a preferred embodiment, an oxidizing step is provided between any two dehydrogenating steps connected.

In the dehydrogenating step, ethylbenzene is dehydrogenated to produce styrene and hydrogen. Ethylbenzene to be introduced into this dehydrogenating step is commonly mixed with steam to use. Mixing ratio of steam to ethylbenzene is usually in the range of 1 to 15 in molar ratio, preferably 1 to 10.

As an apparatus to be used for the dehydrogenating step, a fixed bed apparatus packed with a dehydrogenation catalyst is usually used.

Therefore, the dehydrogenation reaction of the invention is preferably a fixed bed-passing reaction wherein the above-described raw material is passed as a gas through a fixed bed catalyst reactor.

The reaction temperature is usually 500° C. or higher, preferably 550° C. or higher, and is usually 700° C. or lower, preferably 670° C. or lower. As a means to realize the above-described reaction temperature, there is usually employed a method of previously heating the raw materials-mixed gas to about the reaction temperature, then introducing the heated gas into the reactor. The pressure is usually in the range of from 0.0049 to 0.98 MPa. Since the dehydrogenation reaction of ethylbenzene is an endothermic reaction, the temperature within the reactor decreases with the progress of the reaction.

Constituents of the dehydrogenation catalyst are not particularly limited, but there may usually be used those disclosed in Japanese Patent Laid-Open No. 130531/1985, that is, iron-based catalysts containing an alkali metal or an alkaline earth metal or the iron-based catalysts further containing other metals such as zirconium, tungsten, molybdenum, vanadium and chromium. Of these, potassium-containing, iron-based catalysts which contain iron oxide as a major component and potassium oxide and, if desired, the above-described or other metals are preferred. As one example, there are illustrated those which are disclosed in Japanese Patent Laid-Open No. 277030/1992, that is, a catalyst which contains iron oxide and potassium oxide as major components and titanium oxide as a co-catalyst component.

With continuation of the dehydrogenation reaction, the catalyst is deteriorated with the elapse of time. Deterioration of the catalyst in this case means that, in the case of, for example, potassium-containing, iron-based catalysts, potassium flies off, that is, potassium is released from the catalyst and flies off entrained with the reacted gas.

The catalyst deteriorated with the elapse of time shows not only a reduced activity but a reduced styrene selectivity. One factor of this phenomenon is that the catalyst deteriorated with the elapse of time functions to convert hydrocarbons such as styrene to carbon dioxide by the steam reforming reaction. Another factor is that the resultant carbon dioxide in turn functions as a catalyst poison.

The steam reforming reaction takes place in the vicinity of the inlet of a reactor for the dehydrogenating step, that is, in the high-temperature portion of the catalyst layer.

In the case of using the above-described potassium-containing, iron-based catalyst for the process of the invention for producing styrene, it is preferred to use, as the dehydrogenation catalyst, a catalyst-packed bed provided in the reactor in which bed a catalyst showing a lower potassium-flying rate is located in the upstream side of the passage of reacted gas. Specifically, it is possible to use one kind of a dehydrogenation catalyst showing a lower potassium-flying rate, or to use a catalyst showing a lower potassium-flying rate in the upstream side and one or more catalysts showing a relatively higher potassium-flying rate than that of the catalyst in the downstream side.

In the case of using two or more dehydrogenation catalysts different from each other in potassium-flying rate, it is more preferred to use a catalyst with a relatively less activity in the upstream side and a catalyst with a relatively more activity in the downstream side.

Use of the above-described catalyst enables to continue production of styrene over a long period of time with maintaining a high activity and a high selectivity.

Here, potassium-flying rate and activity can be measured in the following manner.
Method for Measuring Flying Rate of Potassium:

A reaction tube of 21 mm in inside diameter is fit with a tube of 4 mm in outside diameter for inserting a thermocouple, and 24 ml of an oxidation catalyst of about 3 mm in particle size is charged thereinto, followed by charging 7 ml of a dehydrogenation catalyst of about 3 to about 4 mm in particle size into the downstream side of the reaction tube. As the oxidation catalyst, the catalyst prepared by the process disclosed in Example 1 of Japanese Patent Laid-Open No. 225140/1986, which comprises a carrier of alumina supporting thereon 0.2% by weight of platinum, 0.5% by weight of tin and 0.2% by weight of lithium, is used.

This reaction tube is placed in an electric furnace, and heated while introducing thereinto nitrogen at a rate of 20 ml/min. At a point when the inlet temperature of the dehydrogenation catalyst layer reaches 550° C., the nitrogen is changed to steam (1.5 g/min).

Then, at a point when the inlet temperature of the dehydrogenation catalyst layer reaches 600° C., a mixed gas of ethylbenzene, styrene and hydrogen and a mixed gas of air and nitrogen are respectively fed to the reaction tube to conduct oxidation reaction of hydrogen in the oxidation catalyst layer and dehydrogenation reaction of ethylbenzene in the succeeding dehydrogenation catalyst layer. The feed gas has a composition of ethylbenzene:styrene:steam:hydrogen:oxygen:nitrogen= 1.0:0.43:11.4:0.39:0.14:1.6 in molar ratio. The reaction is conducted for 2000 hours at a temperature of 640° C. and at a pressure of 0.065 MPa in the dehydrogenation catalyst layer and at an LHSV of sum of ethylbenzene and styrene to the oxidation catalyst of 3.5 hr$^{-1}$. After completion of the reaction, the dehydrogenation catalyst is taken out. The atomic ratio of potassium to iron of the dehydrogenation catalyst is measured before and after the reaction according to an atomic absorption method.

The flying rate of potassium is calculated according to the following formula (1):

$$\text{Potassium-flying rate}=(X-Y)/X \times 100(\%) \qquad (1)$$

(wherein X represents an atomic ratio (%) of potassium to iron in the dehydrogenation catalyst before being subjected to the reaction, and Y represents an atomic ratio (%) of potassium to iron in the dehydrogenation catalyst after being subjected to the reaction).
Method for Measuring Activity:

A reaction tube of 21 mm in inside diameter is fit with a tube of 4 mm in outside diameter for inserting a thermocouple, and 70 ml of a dehydrogenation catalyst of about 3 to about 4 mm in particle size is charged into the reaction tube. This reaction tube is placed in an electric furnace, and heated while introducing thereinto nitrogen at a rate of 20 ml/min. At a point when the inlet temperature of the dehydrogenation catalyst layer reaches 550° C., the nitrogen is changed to steam (1.5 g/min). Further, at a point when the inlet temperature of the dehydrogenation catalyst layer reaches 600° C., the steam is changed to a mixed gas of ethylbenzene and steam (ethylbenzene:steam=1:8 (molar ratio)), followed by conducting the reaction by maintaining the pressure at 0.07 MPa, the LHSV of ethylbenzene at 1 hr$^{-1}$ and the temperature of the catalyst layer at 600° C. 300 hours after the initiation of the reaction, composition of the reaction-produced gas is analyzed by gas chromatography, and the conversion of ethylbenzene is calculated according to the following formula (2):

$$\text{Conversion of ethylbenzene}=(L-M)/L \times 100(\%) \qquad (2)$$

(wherein L represents a mol number of ethylbenzene introduced into the reaction tube, and M represents a mol number of ethylbenzene effused from the reaction tube).

The conversion of ethylbenzene is taken as the catalyst activity.

The flying rate of the catalyst showing a lower potassium-flying rate is 15% or less, preferably 10% or less, more preferably 8% or less, in terms of the value measured and calculated in the above-described manner. The catalyst showing a lower potassium-flying rate has the activity-showing value of preferably 60% or more, more preferably 65% or more in terms of the activity measured and calculated in the above-described manner.

The reacted gas effused from the dehydrogenating step usually contains ethylbenzene, styrene, hydrogen and steam, and its temperature is lower than that at the inlet of the dehydrogenating step. Molar ratio of hydrogen to styrene is usually in the range of from 1.0 to 1.3.

The reacted gas effused from the above-described dehydrogenating step may be introduced into another dehydrogenating step or into an oxidizing step.

In the case of providing an oxidizing step between any of two dehydrogenating steps connected to each other for the process of the invention for producing styrene, that is, in the case where a first dehydrogenating step, an oxidizing step and a second dehydrogenating step are connected in series, the reacted gas effused from the first dehydrogenating step is introduced into the oxidizing step.

Here, the oxidizing step is a step where hydrogen is selectively combusted. The mixture fed to the oxidizing step contains oxygen in order to combust hydrogen. As a source of oxygen, any of oxygen-containing gases may be used with no limitation, and there are illustrated, for example, air, diluted air, air enriched with oxygen and inert gas-diluted oxygen. There are no limitations as to a method for feeding an oxygen-containing gas. For example, it is possible to feed the oxygen-containing gas to the reacted gas effused from the dehydrogenating step and introduce the thus mixed gas into the oxidizing step, or to feed the oxygen-containing gas to the oxidizing step.

Apparatus to be used for the oxidizing step is not particularly limited, and a fixed bed reaction apparatus packed with a solid oxidation catalyst is commonly used.

As the oxidation catalyst, any one may be employed that can selectively combust hydrogen in the co-presence of styrene and ethylbenzene. Usually, a noble metal-based oxidation catalyst is used. Specifically, there are illustrated a catalyst disclosed in Japanese Patent Laid-Open No. 130531/1985, that is, a catalyst containing platinum and potassium, or containing platinum, tin and potassium; and a catalyst disclosed in Japanese Patent Laid-Open No. 225140/1986, that is, a catalyst containing an alkali metal or alkaline earth metal, the group 4A element such as germanium, tin or lead, and a noble metal. In addition, a catalyst disclosed in Japanese Patent Laid-Open No. 298678/1994, that is, a tin catalyst or a catalyst containing tin and an alkali metal, and a catalyst disclosed in 322303/1999, that is, a catalyst containing platinum and niobium or tantalum may also be used.

The reacted gas effused from the oxidizing step has been heated by the heat generated due to oxidation reaction of hydrogen. The temperature of this gas is usually in the range of from 550 to 670° C.

The reacted gas effused from the oxidizing step is introduced into the second dehydrogenating step.

Apparatus, catalyst, reaction conditions, etc. for the second dehydrogenating step may freely be selected from those described with respect to the above-described dehydrogenating step, and the second dehydrogenating step can be conducted independently from the first dehydrogenating step.

The above-described dehydrogenation catalyst is usually deteriorated by oxygen. Therefore, it is preferred for the gas effused from the oxidizing step substantially not to contain oxygen. As a means for this, there is illustrated, for example, a technique of adjusting the amount of oxygen to be fed to the oxidizing step.

In addition, in the second dehydrogenating step, too, a steam reforming reaction proceeds with deterioration of the catalyst with the elapse of time. As is the same as described above, the steam reforming reaction takes place markedly in the vicinity of the inlet of the reactor, that is, in the high-temperature portion of the catalyst layer. Further, the steam reforming reaction proceeds more markedly when the amount of hydrogen to styrene is 0.8 or less, particularly 0.5 or less, in terms of molar ratio.

Accordingly, the steam reforming reaction takes place particularly markedly in the second dehydrogenating step.

As is described above, hydrocarbons such as styrene are converted to carbon dioxide by the steam reforming reaction, thus selectivity of styrene being decreased. Generated carbon dioxide in turn functions as a poison for the dehydrogenation catalyst and, as a result, conversion of ethylbenzene is decreased.

According to the invention, production of styrene can be continued with maintaining the activity and the selectivity at levels of initial stage of the reaction over a long period of time, by maintaining the carbon dioxide-generating ratio within a definite range. The carbon dioxide-generating ratio is kept at a level of less than 2.1 times, preferably less than 2.0 times, more preferably less than 1.9 times as much as that at the initial stage of the reaction.

The term "initial stage of the reaction" as used herein means the point at which activity of the dehydrogenation catalyst becomes stable after initiation of feeding ethylbenzene to the reactor for the dehydrogenating step. Additionally, activity of the dehydrogenation catalyst usually changes greatly immediately after initiation of feeding ethylbenzene, and becomes stable 1000 to 2000 hours after initiation of feeding ethylbenzene.

The carbon dioxide-generating ratio in the reactor for the dehydrogenating step is determined by sampling the gas at the inlet and the outlet of the dehydrogenation reactor, analyzing respective samples through gas chromatography, and calculating according to the following formula (3):

$$\text{Carbon dioxide-generating ratio} = (Q-P)/(R+S) \times 100(\%) \quad (3)$$

P: mol number of carbon dioxide introduced through the inlet of the reactor for the dehydrogenating step;

Q: mol number of carbon dioxide effused through the outlet of the reactor for the dehydrogenating step;

R: mol number of ethylbenzene introduced through the inlet of the reactor for the dehydrogenating step;

S: mol number of styrene introduced through the inlet of the reactor for the dehydrogenating step.

In the invention, means for maintaining the amount of generated carbon dioxide within a certain range is not particularly limited but, specifically, it is preferred to employ the following embodiments.

As to the amount of hydrogen of the reacted gas to be introduced into the second dehydrogenating step, the lower limit is 0.8 times, preferably 0.9 times, based on styrene, in terms of molar ratio, and the upper limit is 2.0 times, preferably 1.3 times, based on styrene, in terms of molar ratio. Thus, preferred range of the amount is 0.8 to 2.0 times, with more preferred range being 0.9 to 1.3 times. As to the means to realize such amount, there are illustrated, for example, to feed hydrogen to the reacted gas effused from the oxidizing step, to feed hydrogen to the reacted gas to be introduced into the oxidizing step, and to introduce hydrogen into the second dehydrogenating step. These means may be employed alone or in combination. Preferably, hydrogen is fed to the reacted gas to be introduced into the oxidizing step. To feed hydrogen to the reacted gas to be introduced into the oxidizing step also serves to improve selectivity of the combustion reaction of hydrogen in the oxidizing step.

Deterioration of the catalyst causes a reduction in activity and, in order to maintain the yield of the product, it is commonly employed to raise the reaction temperature. As to the point where hydrogen is fed as described above, a point where the reaction temperature reaches 620° C. or above, preferably 630° C. or above, is selected.

As another embodiment for maintaining the amount of generated carbon dioxide at a level within a definite range, it is preferred to use, as the dehydrogenation catalyst, the above-described potassium-containing, iron-based catalyst wherein a catalyst showing a less potassium-flying rate is provided in the upstream side of the passage of reacted gas. Specifically, there are illustrated to use one kind of a dehydrogenation catalyst showing a less potassium-flying rate and to use the catalyst showing a less potassium-flying rate in the upstream side and one or more kinds of a catalyst showing a relatively higher potassium-flying rate than that of the catalyst in the downstream side.

In addition, in the case of using two or more kinds of dehydrogenation catalysts different in the potassium-flying rate, the two or more dehydrogenation catalysts are particularly preferably used in such manner that the catalyst showing a relatively lower activity is used in the upstream side and the catalyst showing a relatively higher activity in the downstream side.

Here, as the flying rate of the catalyst showing a lower potassium-flying rate, the value determined by measuring and calculating according to the method described hereinbefore is usually 15% or less, preferably 10% or less, more preferably 8% or less. The catalyst showing a lower potassium-flying rate has the activity value determined by measuring and calculating in the above-described manner of preferably 60% or more, more preferably 65% or more.

The above-described embodiments may be conducted independently or in combination. Of these, as an embodiment to conduct the embodiment independently, it is preferred to use one kind of the catalyst showing a lower potassium-flying rate or adjust the amount of hydrogen in the reacted gas to be introduced into the second dehydrogenating step within the range of 0.8 to 2.0 times based on styrene in terms of molar ratio.

The steam reforming reaction is markedly depressed by one, or a combination, of the above-described preferred embodiments, thus the amount of generated carbon dioxide being reduced. As a result, reduction in activity and selectivity is markedly depressed even when production of styrene is continued for a long period of time. The process of the invention is an industrially extremely advantageous process for producing styrene.

The second dehydrogenating step of the invention is a dehydrogenating step provided in the downstream of the oxidizing step, as described above. That is, a dehydrogenating step into which a reacted gas having been subjected to the oxidizing step to selectively oxidize hydrogen is to be introduced can be the second dehydrogenating step of the invention. Therefore, in the case where three or more dehydrogenating steps are provided, for example, where a second oxidizing step and a third dehydrogenating step are provided, too, it should be understood that embodiments coinciding with the above-described conditions be within the scope of the invention.

The reacted gas effused from the second dehydrogenating step can be introduced into a product-recovering system to recover ethylbenzene and styrene, with ethylbenzene being recycled to use. If desired, hydrogen can also be recovered and recycled to use.

EXAMPLES

The invention is described in more detail by reference to examples which, however, do not limit the invention in any way. Additionally, in the following Examples and Comparative Examples, the following oxidation catalysts and dehydrogenation catalysts were used.

Oxidation Catalyst (a):

A catalyst containing $Al_2O_3$ carrying thereon 0.2% by weight of Pt, 0.5% by weight of Sn and 0.2% by weight of Li and produced according to Example 1 in Japanese Patent Laid-Open No. 225140/1986 was used.

Oxidation Catalyst (b):

A catalyst containing $Nb_2O_5$ carrying thereon 0.2% by weight of Pt and produced according to Example 8 in Japanese Patent Laid-Open No. 29095/1997 was used.

Dehydrogenation Catalyst (a):

A catalyst prepared according to Example 6 in Japanese Patent Laid-Open No. 277030/1992 was used. A deteriorated dehydrogenation catalyst used was prepared by packing this dehydrogenation catalyst in a reaction tube and passing therethrough a mixed gas of ethylbenzene and steam (molar ratio=1:9) at 640° C. and at an LHSV of 10 $hr^{-1}$ for 3000 hours. This catalyst underwent a reduction in potassium content from 8.2% by weight to 0.17% by weight, which was analyzed according to the atomic absorption method.

Dehydrogenation Catalyst (b):

A potassium-iron-based dehydrogenation catalyst containing Mo, Ce, etc. as co-catalyst components. Particle size: about 4 mm. Content of $Fe_2O_3$:37.7% by weight. K/Fe=0.96 (atomic ratio). Potassium-flying rate: 8%. Conversion of ethylbenzene: 65%.

Dehydrogenation Catalyst (c):

A potassium-iron-based dehydrogenation catalyst containing Mo, Ce, etc. as co-catalyst components. Particle size: about 3 mm. Content of $Fe_2O_3$:52.5% by weight. K/Fe= 0.44. Potassium-flying rate: 26%. Conversion of ethylbenzene: 66%.

Dehydrogenation Catalyst (d):

A potassium-iron-based dehydrogenation catalyst containing Mo, Ce, Ti, etc. as co-catalyst components. Particle size: about 3 mm. Content of $Fe_2O_3$:67% by weight. K/Fe= 0.58 (atomic ratio). Potassium-flying rate: 23%. Conversion of ethylbenzene: 71%.

The conversion of ethylbenzene, selectivity to styrene, ratio of generating carbon dioxide and ratio of generating benzene in the dehydrogenation catalyst layer were respectively calculated according to the following formulae:

$$\text{Conversion of ethylbenzene} = (A-B)/A \times 100(\%)$$

$$\text{Selectivity to styrene} = (C-D)/(A-B) \times 100(\%)$$

$$\text{Ratio of generating carbon dioxide} = (E-F)/(A+D) \times 100(\%)$$

$$\text{Ratio of generating benzene} = (H-J)/(A+D) \times 100(\%)$$

A: Ethylbenzene introduced into the dehydrogenation catalyst layer (mol);
B: Ethylbenzene effused from the reactor (mol);
C: Styrene effused from the reactor (mol);
D: Styrene introduced into the dehydrogenation catalyst layer (mol);
E: Carbon dioxide effused from the reactor (mol);
F: Carbon dioxide introduced into the dehydrogenation catalyst layer (mol);
H: Benzene effused from the reactor (mol);
J: Benzene introduced into the dehydrogenation catalyst layer (mol).

Example 1

A reaction tube of 21 mm in inside diameter was fitted with a thermocouple-introducing tube of 4 mm in outside diameter, and 24 ml of oxidation catalyst (a), 24 ml of deteriorated dehydrogenation catalyst (a) and 36 ml of normal dehydrogenation catalyst (a) were packed, from the upstream side, in the reaction tube in this order to form a catalyst-packed bed containing the oxidation catalyst layer and the dehydrogenation catalyst layers one of which was a deteriorated catalyst layer and the other of which was a normal catalyst layer. Additionally, a space was provided between the oxidation catalyst layer and the dehydrogenation catalyst layer, and a hydrogen-feeding pipe was connected to the space. This reaction tube was placed in an electric furnace and heated while feeding a nitrogen gas at a rate of 20 ml/min. At a point when temperature of the inlet portion of the dehydrogenation catalyst layer reached 550° C., the nitrogen gas was changed to steam (1.5 g/min). Then, at a point when the temperature at the inlet portion of the dehydrogenation catalyst layer reached 600° C., the feed gas was changed to a combination of a mixed gas of ethylbenzene, styrene, steam, hydrogen and carbon dioxide and a mixed gas of air and nitrogen, with feeding hydrogen through the hydrogen-feeding pipe, to thereby conduct selective combustion reaction of hydrogen with the aid of the oxidation catalyst and dehydrogenation reaction of ethylbenzene with the aid of the dehydrogenation catalyst. During the reaction, the temperature at the inlet of the dehydrogenation catalyst layer was kept at 640° C., and the temperature at the outlet of the dehydrogenation catalyst layer was kept at 610° C. The composition of a feed gas to the oxidation catalyst layer was ethylbenzene:styrene:steam:hydrogen:oxygen:nitrogen:carbon dioxide= 1.0:0.43:11.4:0.44:0.16:1.8:0.01 (molar ratio). The feed gas was fed to the reaction tube at a pressure of 0.065 MPa and an LHSV of the sum of ethylbenzene and styrene based on the dehydrogenation catalyst of 1.2 $hr^{-1}$. Hydrogen was fed through the hydrogen-feeding pipe in such amount that the molar ratio of hydrogen to styrene contained in the gas introduced into the dehydrogenation catalyst layer became 1.06.

After 100 hours from the initiation of the reaction, the outlet gas of the oxidation catalyst layer and the outlet gas of the reactor were analyzed, and the results were shown in Table 1.

Data on the initial stage reaction were obtained in the following manner. That is, a reaction tube of 21 mm in inside diameter was fitted with a thermocouple-introducing tube of 4 mm in outside diameter, and 24 ml of oxidation catalyst (a) and 60 ml of normal dehydrogenation catalyst (a) were packed, from the upstream side, in the reaction tube in this order to form a catalyst-packed bed having the oxidation catalyst layer and the dehydrogenation catalyst layer. Additionally, a space was provided between the oxidation catalyst layer and the dehydrogenation catalyst layer, and a hydrogen-feeding pipe was connected to the space. This reaction tube was placed in an electric furnace and heated while feeding a nitrogen gas at a rate of 20 ml/min. At a point when temperature of the inlet portion of the dehydrogenation catalyst layer reached 550° C., the nitrogen gas was changed to steam (1.5 g/min). Then, at a point when the temperature at the inlet portion of the dehydrogenation catalyst layer reached 600° C., the feed gas was changed to a combination of a mixed gas of ethylbenzene, styrene, steam, hydrogen and carbon dioxide and a mixed gas of air and nitrogen, with feeding hydrogen through the hydrogen-feeding pipe, to thereby conduct selective combustion reaction of hydrogen with the aid of the oxidation catalyst and dehydrogenation reaction of ethylbenzene with the aid of the dehydrogenation catalyst. During the reaction, the temperature at the inlet of the dehydrogenation catalyst layer was kept at 640° C., and the temperature at the outlet of the dehydrogenation catalyst layer was kept at 610° C. The composition of a feed gas to the oxidation catalyst layer was ethylbenzene:styrene:steam:hydrogen:oxygen:nitrogen:carbon dioxide= 1.0:0.43:11.4:0.44:0.16:1.8:0.01 (molar ratio). The feed gas was fed to the reaction tube at a pressure of 0.065 MPa and an LHSV of the sum of ethylbenzene and styrene based on the dehydrogenation catalyst of 10 $hr^{-1}$. Hydrogen was fed through the hydrogen-feeding pipe in such amount that the molar ratio of hydrogen to styrene contained in the gas introduced into the dehydrogenation catalyst layer became 1.06.

100 hours after initiation of the reaction, the activity of the dehydrogenation catalyst became stable and, in order to measure the carbon dixoxide-generating ratio in the initial stage of the reaction, only LHSV of the sum of ethylbenzene and styrene based on the dehydrogenation catalyst was changed to 1.2 $hr^{-1}$ while maintaining the temperature and the pressure at the same levels. 100 hours after the change, the gas effused from the oxidation catalyst layer and the outlet gas of the reaction tube were collected, and their compositions were analyzed according to gas chromatography. The results thus obtained were shown in Table 2.

Comparative Example 1

The reaction was conducted in the same manner as in Example 1 except for not feeding hydrogen through the hydrogen-feeding pipe. Results thus obtained are shown in Table 1. Additionally, molar ratio of hydrogen to styrene in the gas introduced into the dehydrogenation catalyst layer was 0.6.

Data for the initial stage reaction were obtained in the following manner. That is, the reaction was conducted in the same manner as that for obtaining the data for the initial stage reaction in Example 1 except for not feeding hydrogen through the hydrogen-feeding pipe. Results thus obtained are shown in Table 2. Additionally, molar ratio of hydrogen to styrene in the gas introduced into the dehydrogenation catalyst layer was 0.6.

Comparative Example 2

Reaction was conducted in the same manner as in Example 1 except for increasing the amount of oxygen in the gas fed to the oxidation catalyst layer and not feeding hydrogen through the hydrogen-feeding pipe. Results are shown in Table 1. Additionally, molar ratio of hydrogen to styrene in the gas introduced into the dehydrogenation catalyst layer was 0.28.

Data for the initial stage reaction were obtained in the following manner. That is, the reaction was conducted in the same manner as that for obtaining the data for the initial stage reaction in Example 1 except for increasing the amount of oxygen in the gas introduced into the oxidation catalyst layer and not feeding hydrogen through the hydrogen-feeding pipe. Results thus obtained are shown in Table 2. Additionally, molar ratio of hydrogen to styrene in the gas introduced into the dehydrogenation catalyst layer was 0.28.

TABLE 1

|  | Example 1 | Com. Example 1 | Com. Example 2 | Blank |
|---|---|---|---|---|
| Conversion of ethylbenzene | 28.9 | 23.9 | 20.8 | — |
| Selectivity to styrene | 93.6 | 92.2 | 90.0 | — |
| Ratio of generating carbon dioxide | 3.3 | 3.9 | 4.7 | 2.2 |
| Ratio of carbon | 1.4 | 2.1 | 3.1 | — |

TABLE 1-continued

|  | Example 1 | Com. Example 1 | Com. Example 2 | Blank |
|---|---|---|---|---|
| dioxide-generating ratio to that of the initial stage of the reaction |  |  |  |  |
| Benzene-generating ratio | 0.45 | 0.51 | 0.62 | — |

(Notes) "Blank" was a result obtained by conducting the same procedures as in Example 1 except for packing porcelain Raschig rings of 3 mm in diameter in place of the dehydrogenation catalyst and not feeding hydrogen through the hydrogen-feeding pipe. "Ratio of carbon dioxide-generating ratio to that of the initial stage of the reaction" is a value calculated with subtracting the amount generated in the blank test. For example, the ratio of carbon dioxide-generating ratio to that of the initial stage of the reaction in Example 1 can be calculated by (3.3−2.2)/(3.0−2.2).

TABLE 2

|  | Example 1 In the Initial Stage of the reaction | Com. Example 1 In the Initial Stage of the reaction | Com. Example 2 In the Initial Stage of the reaction | Blank In the Initial Stage of the reaction |
|---|---|---|---|---|
| Conversion of ethylbenzene | 42.9 | 43.8 | 44.7 | — |
| Selectivity to styrene | 95.1 | 95.2 | 95.2 | — |
| Ratio of generating carbon dioxide | 3.0 | 3.0 | 3.0 | 2.2 |
| Benzene-generating ratio | 0.34 | 0.34 | 0.34 | — |

Example 2

Reaction was conducted in the same manner as in Example 1 except for using oxidation catalyst (b) in place of oxidation catalyst (a) and feeding hydrogen through the hydrogen-feeding pipe in such amount that the molar ratio of hydrogen to styrene in the gas introduced into the dehydrogenation catalyst layer became 1.0. Results thus obtained are shown in Table 3.

Data for the initial stage reaction were obtained in the following manner. That is, the reaction was conducted in the same manner as that for obtaining the data for the initial stage reaction in Example 1 except for using oxidation catalyst (b) in place of oxidation catalyst (a) and feeding hydrogen through the hydrogen-feeding pipe in such amount that the molar ratio of hydrogen to styrene in the gas introduced into the dehydrogenation catalyst layer became 1.0. Results thus obtained are shown in Table 4.

Comparative Example 3

Reaction was conducted in the same manner as in Comparative Example 1 except for using oxidation catalyst (b) in place of oxidation catalyst (a). Results are shown in Table 3. Additionally, molar ratio of hydrogen to styrene in the gas introduced into the dehydrogenation catalyst layer was 0.59.

Data for the initial stage reaction were obtained in the following manner. That is, the reaction was conducted in the same manner as that for obtaining the data for the initial stage reaction in Comparative Example 1 except for using oxidation catalyst (b) in place of oxidation catalyst (a). Results thus obtained are shown in Table 4. Additionally, molar ratio of hydrogen to styrene in the gas introduced into the dehydrogenation catalyst layer was 0.59.

Comparative Example 4

Reaction was conducted in the same manner as in Comparative Example 2 except for using oxidation catalyst (b) in place of oxidation catalyst (a). Results are shown in Table 3. Additionally, molar ratio of hydrogen to styrene in the gas introduced into the dehydrogenation catalyst layer was 0.29.

Data for the initial stage reaction were obtained in the following manner. That is, the reaction was conducted in the same manner as that for obtaining the data for the initial stage reaction in Comparative Example 2 except for using oxidation catalyst (b) in place of oxidation catalyst (a). Results thus obtained are shown in Table 4. Additionally, molar ratio of hydrogen to styrene in the gas introduced into the dehydrogenation catalyst layer was 0.29.

TABLE 3

|  | Example 2 | Com. Example 3 | Com. Example 4 | Blank |
|---|---|---|---|---|
| Conversion of ethylbenzene | 31.0 | 27.1 | 25.0 | — |
| Selectivity to styrene | 94.0 | 93.1 | 92.2 | — |
| Ratio of generating carbon dioxide | 3.2 | 3.7 | 4.3 | 2.2 |
| Ratio of carbon dioxide-generating ratio to that of the initial stage of the reaction | 1.3 | 2.1 | 3.0 | — |
| Benzene-generating ratio | 0.44 | 0.50 | 0.61 | — |

TABLE 4

|  | Example 2 In the Initial Stage of the reaction | Com. Example 3 In the Initial Stage of the reaction | Com. Example 4 In the Initial Stage of the reaction | Blank In the Initial Stage of the reaction |
|---|---|---|---|---|
| Conversion of ethylbenzene | 45.5 | 46.8 | 47.9 | — |
| Selectivity to styrene | 95.5 | 95.6 | 95.6 | — |
| Ratio of generating carbon dioxide | 3.0 | 2.9 | 2.9 | 2.2 |
| Benzene-generating ratio | 0.34 | 0.34 | 0.34 | — |

Example 3

A reaction tube of 21 mm in inside diameter was fitted with a thermocouple-introducing tube of 4 mm in outside diameter, and 24 ml of oxidation catalyst (a) and 60 ml of dehydrogenation catalyst (b) were packed, from the upstream side, in the reaction tube in this order to form a two-layered catalyst bed. Additionally, a little space was provided between the oxidation catalyst layer and the dehydrogenation catalyst layer so as to collect a gas effused from the oxidation catalyst layer. This reaction tube was placed in an electric furnace and heated while feeding a nitrogen gas at a rate of 20 ml/min. At a point when temperature of the inlet portion of the dehydrogenation catalyst layer reached 550° C., the nitrogen gas was changed to steam (1.5 g/min).

Then, at a point when the temperature at the inlet portion of the dehydrogenation catalyst layer reached 600° C., the feed gas was changed to a mixed gas of ethylbenzene:styrene:steam:hydrogen:oxygen:nitrogen:carbon dioxide= 1.0:0.43:11.4:0.44:0.16:1.8:0.01 (molar ratio) to thereby initiate dehydrogenation reaction of ethylbenzene. The mixed gas was fed to the reaction tube at a pressure of 0.065 MPa and at an LHSV of the sum of ethylbenzene and styrene based on the dehydrogenation catalyst of 10 $hr^{-1}$. The dehydrogenation catalyst layer was kept at 640° C. in the inlet temperature and 610° C. in outlet temperature.

After 100 hours from the initiation of the reaction, the activity of the dehydrogenation catalyst became stable and, in order to measure the carbon dioxide-generating ratio in the initial stage of the reaction, only LHSV of the sum of ethylbenzene and styrene based on the dehydrogenation catalyst was changed to 1.2 $hr^{-1}$ while maintaining the temperature and the pressure at the same levels. 100 hours after the change, the gas effused from the oxidation catalyst layer and the outlet gas of the reaction tube were collected, and their compositions were analyzed according to gas chromatography. The results thus obtained were shown in Table 6.

After collecting the gases, LHSV was restored to 10 $hr^{-1}$, and the reaction was continued. At a time when 3000 hours passed from the initiation of the reaction, only LHSV of the sum of ethylbenzene and styrene based on the dehydrogenation catalyst was changed to 1.2 $hr^{-1}$. 100 hours after the change, the gas effused from the oxidation catalyst layer and the outlet gas of the reaction tube were collected, and their compositions were analyzed according to gas chromatography. The results thus obtained were shown in Table 5.

Comparative Example 5

Dehydrogenation reaction of ethylbenzene was conducted in absolutely the same manner as in Example 3 except for using dehydrogenation catalyst (c) in place of dehydrogenation catalyst (b) in Example 3. Results thus obtained are shown in Tables 5 and 6.

TABLE 5

|  | Example 3 | Com. Example 5 | Blank |
|---|---|---|---|
| Conversion of ethylbenzene | 42.0 | 23.9 | — |
| Selectivity to styrene | 95.3 | 92.2 | — |
| Ratio of generating carbon dioxide | 3.0 | 3.9 | 2.2 |
| Ratio of carbon dioxide-generating ratio to that of the initial stage of the reaction | 1.1 | 2.4 | — |
| Benzene-generating ratio | 0.34 | 0.51 | — |

TABLE 6

|  | Example 3 In the Initial Stage of the reaction | Com. Example 5 In the Initial Stage of the reaction | Blank |
|---|---|---|---|
| Conversion of ethylbenzene | 43.1 | 43.8 | — |
| Selectivity to styrene | 95.3 | 95.2 | — |

TABLE 6-continued

|  | Example 3 In the Initial Stage of the reaction | Com. Example 5 In the Initial Stage of the reaction | Blank |
|---|---|---|---|
| Ratio of generating carbon dioxide | 2.9 | 2.9 | 2.2 |
| Benzene-generating ratio | 0.34 | 0.34 | — |

Example 4

A reaction tube of 21 mm in inside diameter was fitted with a thermocouple-introducing tube of 4 mm in outside diameter, and 24 ml of oxidation catalyst (a), 24 ml of dehydrogenation catalyst (b), and 36 ml of dehydrogenation catalyst (d) were packed, from the upstream side, in the reaction tube in this order to form a three-layered catalyst bed. Additionally, a little space was provided between the oxidation catalyst layer and the dehydrogenation catalyst layer so as to collect a gas effused from the oxidation catalyst layer. This reaction tube was placed in an electric furnace and heated while feeding a nitrogen gas at a rate of 20 ml/min. At a point when temperature of the inlet portion of the dehydrogenation catalyst layer reached 550° C., the nitrogen gas was changed to steam (1.5 g/min). Then, at a point when the temperature at the inlet portion of the dehydrogenation catalyst layer reached 600° C., the feed gas was changed to a mixed gas of ethylbenzene:styrene:steam:hydrogen:oxygen:nitrogen:carbon dioxide= 1.0:0.43:11.4:0.44:0.16:1.8:0.01 (molar ratio) to thereby initiate dehydrogenation reaction of ethylbenzene. The mixed gas was fed to the reaction tube at a pressure of 0.065 MPa and at an LHSV of the sum of ethylbenzene and styrene based on the dehydrogenation catalyst of 10 $hr^{-1}$. The dehydrogenation catalyst layer was kept at 640° C. in the inlet temperature and 610° C. in outlet temperature.

After 100 hours from the initiation of the reaction, the activity of the dehydrogenation catalyst became stable and, in order to measure the carbon dioxide-generating ratio in the initial stage of the reaction, only LHSV of the sum of ethylbenzene and styrene based on the dehydrogenation catalyst was changed to 1.2 $hr^{-1}$ while maintaining the temperature and the pressure at the same levels. 100 hours after the change, the gas effused from the oxidation catalyst layer and the outlet gas of the reaction tube were collected, and their compositions were analyzed according to gas chromatography. The results thus obtained were shown in Table 8.

After collecting the gases, LHSV was restored to 10 $hr^{-1}$, and the reaction was continued. At a time when 3000 hours passed from the initiation of the reaction, only LHSV of the sum of ethylbenzene and styrene based on the dehydrogenation catalyst was again changed to 1.2 $hr^{-1}$. 100 hours after the change, the gas effused from the oxidation catalyst layer and the outlet gas of the reaction tube were collected, and their compositions were analyzed according to gas chromatography. The results thus obtained were shown in Table 7.

Comparative Example 6

Dehydrogenation reaction of ethylbenzene was conducted in absolutely the same manner as in Example 4 except for using, as the dehydrogenation catalyst, 60 ml of dehydrogenation catalyst (d) in place of 24 ml of dehydrogenation catalyst (b) and 36 ml of dehydrogenation catalyst (d) in Example 4. Results thus obtained are shown in Tables 7 and 8.

TABLE 7

|  | Example 4 | Com. Example 6 | Blank |
|---|---|---|---|
| Conversion of ethylbenzene | 50.3 | 29.0 | — |
| Selectivity to styrene | 95.3 | 92.5 | — |
| Ratio of generating carbon dioxide | 3.3 | 4.2 | 2.2 |
| Ratio of carbon dioxide-generating ratio to that of the initial stage of the reaction | 1.2 | 2.5 | — |
| Benzene-generating ratio | 0.34 | 0.50 | — |

TABLE 8

|  | Example 4 In the Initial Stage of the reaction | Com. Example 6 In the Initial Stage of the reaction | Blank |
|---|---|---|---|
| Conversion of ethylbenzene | 51.4 | 55.3 | — |
| Selectivity to styrene | 95.3 | 95.2 | — |
| Ratio of generating carbon dioxide | 3.1 | 3.0 | 2.2 |
| Benzene-generating ratio | 0.33 | 0.34 | — |

Example 5

In a process for producing styrene wherein three dehydrogenating steps were provided and an oxidizing step was provided between the first and the second dehydrogenating steps and between the second and the third dehydrogenating steps, the effect of feeding hydrogen to the reacted gases introduced into the oxidizing steps in such amount that carbon dioxide-generating ratios in the second and the third dehydrogenating steps were maintained at a level of less than 2 times as much as that in the initial stage of the reaction was confirmed by simulation through calculation. Additionally, "gPROMS" made by Process Systems Enterprise Limited was used as a solver, and all of the reactors for the dehydrogenating steps were assumed to be packed with normal, non-deteriorated dehydrogenation catalyst (a) and oxidation catalyst (a).

According to the calculation under the assumed conditions, carbon dioxide-generating ratios in the second and the third dehydrogenating steps became at a level two times or more as much as those in the initial stage of the reaction respectively after operating for 7500 hours, and hence feeding of hydrogen to the reacted gas introduced into the oxidizing steps provided at the upstream side of respective dehydrogenating steps was initiated. Since carbon dioxide-generating ratios in the second and the third dehydrogenating steps again became at a level two times or more as much as those in the initial stage of the reaction respectively after operating for 9500 hours, 11500 hours, and 13000 hours, the amount of hydrogen fed to the reacted gas to be introduced into the oxidizing steps was increased. Results thus obtained are shown in Table 9.

Comparative Example 7

Absolutely the same simulation as in Example 5 was conducted except for not feeding hydrogen to the reacted gas to be introduced into the oxidizing steps in Example 5. Results are shown in Table 9.

By controlling the carbon dioxide-generating ratio at a level less than 2.1 times that in the initial stage of the reaction, styrene can be produced with maintaining a high yield and a high selectivity even after operating for 7500 hours.

TABLE 9

|  |  |  | Operating Period (hr) | | | | | |
|---|---|---|---|---|---|---|---|---|
|  |  |  | 2000 | 5000 | 7500 | 9500 | 11500 | 13000 |
| (1) | Molar ratio of hydrogen to styrene in the gas fed to the second dehydrogenating step | Ex.5 | 0.44 | 0.45 | 0.60 | 0.70 | 0.80 | 0.90 |
|  |  | Com. Ex.7 | 0.44 | 0.45 | 0.45 | 0.46 | 0.47 | 0.48 |
| (2) | Ratio of carbon dioxide-generating ratio in the second dehydrogenating step to that of the initial stage of the reaction | Ex.5 | 1.19 | 1.56 | 1.73 | 1.82 | 1.84 | 1.82 |
|  |  | Com. Ex.7 | 1.19 | 1.56 | 2.01 | 2.37 | 2.71 | 2.95 |
| (3) | Molar ratio of hydrogen to styrene in the gas fed to the third dehydrogenating step | Ex.5 | 0.42 | 0.44 | 0.60 | 0.70 | 0.80 | 0.90 |
|  |  | Com. Ex.7 | 0.42 | 0.44 | 0.46 | 0.50 | 0.55 | 0.59 |
| (4) | Ratio of carbon dioxide-generating ratio in the third dehydrogenating step to that of the initial stage of the reaction | Ex.5 | 1.27 | 1.65 | 1.80 | 1.73 | 1.59 | 1.47 |
|  |  | Com. Ex.7 | 1.27 | 1.65 | 2.10 | 2.18 | 2.15 | 2.11 |
| (5) Reaction results of the whole reaction steps | (5-1) Conversion of ethylbenzene | Ex.5 | 70.7 | 70.5 | 70.6 | 69.8 | 68.3 | 66.8 |
|  |  | Com. Ex.7 | 70.7 | 70.5 | 69.8 | 68.4 | 66.5 | 64.8 |
|  | (5-2) Selectivity to styrene | Ex.5 | 95.3 | 94.7 | 94.0 | 93.6 | 93.2 | 92.8 |
|  |  | Com. Ex.7 | 95.3 | 94.7 | 93.9 | 93.4 | 92.8 | 92.4 |
|  | (5-3) Yield of styrene | Ex.5 | 67.4 | 66.8 | 66.4 | 65.3 | 63.7 | 62.0 |

TABLE 9-continued

|  | Operating Period (hr) | | | | | |
| --- | --- | --- | --- | --- | --- | --- |
|  | 2000 | 5000 | 7500 | 9500 | 11500 | 13000 |
| Com. Ex.7 | 67.4 | 66.8 | 65.6 | 63.9 | 61.8 | 59.9 |

While the invention has been described in detail and with reference to specific embodiments thereof, it will be apparent to one skilled in the art that various changes and modifications can be made therein without departing from the spirit and scope thereof.

This application is based on Japanese Patent Applications No. 248094/2000 filed on Aug. 18, 2000, No. 269612/2000 filed on Sep. 6, 2000, and No. 269613/2000 filed on Sep. 6, 2000, the entire contents thereof being hereby incorporated by reference Industrial Applicability According to the invention, in the process of producing a styrene from ethylbenzene containing the combination of dehydrogenation reaction and oxidation reaction, styrene can be produced in a high yield over a long period of time.

What is claimed is:

1. A process for producing styrene by dehydrogenation of ethylbenzene, which comprises the steps of (i) feeding a raw material gas comprising ethylbenzene and steam to a first dehydrogenating step to produce a reacted gas comprising ethylbenzene, styrene and hydrogen in the presence of a dehydrogenation catalyst, (ii) feeding the reacted gas obtained in the first dehydrogenating step to an oxidizing step to combust at least part of hydrogen in the presence of an oxidation catalyst, and (iii) feeding the reacted gas obtained in the oxidizing step to a second dehydrogenating step to produce styrene from ethylbenzene in the presence of the dehydrogenation catalyst, with maintaining the carbon dioxide-generating ratio in the second dehydrogenating step at a level less than 2.1 times that at an initial stage of the reaction of the second dehydrogenation step.

2. The process as claimed in claim 1, wherein the carbon dioxide-generating ratio is maintained at a level less than 2.0 times that at the initial stage of the reaction of the second dehydrogenation step.

3. The process as claimed in claim 1 or 2, wherein the reacted gas to be fed to the second dehydrogenating step has a molar ratio of hydrogen to styrene in the range of from 0.8 to 2.0.

4. The process as claimed in claim 1 or 2, wherein the reacted gas to be fed to the second dehydrogenating step has a molar ratio of hydrogen to styrene in the range of from 0.9 to 1.3.

5. The process as claimed in claim 1 or 2, wherein the reacted gas generated in the first dehydrogenating step is mixed with oxygen and hydrogen, and fed to the oxidizing step.

6. The process as claimed in claim 1 or 2, wherein the reacted gas generated in the oxidizing step is mixed with hydrogen, and fed to the second dehydrogenating step.

7. The process as claimed in claim 1 or 2, wherein the catalyst in the second dehydrogenating step is a potassium-containing, iron-based catalyst in which the ratio of potassium to iron in a 5% by weight portion of the catalyst in an inlet portion of the reactor is 15% or less of the ratio of potassium to iron in the remaining portion of the catalyst.

8. The process as claimed in claim 1 or 2, wherein the catalyst in the second dehydrogenating step is a potassium-containing, iron-based catalyst in which the ratio of potassium to iron in a 10% by weight portion of the catalyst in an inlet portion of the reactor is 15% or less of the ratio of potassium to iron in the remaining portion of the catalyst.

9. The process as claimed in claim 1 or 2, wherein the temperature of the reacted gas to be fed to the second dehydrogenating step is 620° C. or higher than that.

10. The process as claimed in claim 1 or 2, wherein the catalyst in the second dehydrogenating step is a potassium-containing, iron-based catalyst wherein a catalyst having a lower potassium-flying rate is used in the upstream side of the catalyst in the second dehydrogenating step.

11. The process as claimed in claim 1 or 2, wherein two kinds of dehydrogenation catalysts different from each other in potassium-flying rate are used in the dehydrogenating step of or after the second dehydrogenating step, and one catalyst showing a relatively lower potassium-flying rate is used in the upstream side and the other catalyst showing a relatively higher potassium-flying rate is used on the downstream side.

12. The process as claimed in claim 1 or 2, further comprising subsequent to the second dehydrogenating step a second oxidizing step followed by a third dehydrogenating step.

13. A process for producing styrene by dehydrogenation of ethylbenzene, which comprises:

feeding a gas comprising ethylbenzene, styrene, and hydrogen into a dehydrogenation stage comprising a first catalyst which comprises potassium and iron and a second catalyst which comprises potassium and iron;

wherein the first catalyst is located in the upstream portion of the dehydrogenation stage and the second catalyst is located in the downstream portion of the dehydrogenation stage; and wherein the first catalyst has a lower potassium-flying rate than the second catalyst.

14. The process as claimed in claim 13, which further comprises feeding a raw material gas comprising ethylbenzene and steam to a first dehydrogenating step to produce a reacted gas comprising ethylbenzene, styrene and hydrogen in the presence of a dehydrogenation catalyst;

feeding a reacted gas obtained in the first dehydrogenating step to an oxidizing step to combust at least part of hydrogen in the presence of an oxidation catalyst to produce said gas.

15. The process as claimed in claim 14, wherein the reacted gas to be fed to the dehydrogenation stage has a molar ratio of hydrogen to styrene in the range of from 0.8 to 2.0.

16. The process as claimed in claim 14, wherein the reacted gas to be fed to the dehydrogenation stage has a molar ratio of hydrogen to styrene in the range of from 0.9 to 1.3.

17. The process as claimed in claim 14, wherein the reacted gas generated in the first dehydrogenating step is mixed with oxygen and hydrogen, and fed to the oxidizing step.

18. The process as claimed in claim 14, wherein the gas generated in the oxidizing step is mixed with hydrogen, and fed to the second dehydrogenation stage.

19. The process as claimed in claim 14, further comprising subsequent to the dehydrogenation stage a second oxidizing step followed by a third dehydrogenating step.

* * * * *